US010603084B1

(12) United States Patent
Sanders et al.

(10) Patent No.: US 10,603,084 B1
(45) Date of Patent: Mar. 31, 2020

(54) SYSTEMS FOR TREATMENT OF SPINAL DEFORMITIES

(71) Applicants: Albert E. Sanders, San Antonio, TX (US); James O. Sanders, Pittsford, NY (US); Ronald G. Blackman, Oakland, CA (US); Robert B. More, Austin, TX (US); Brian Snyder, Westwood, MA (US); Grant D. Hogue, San Antonio, TX (US); Ira Zaltz, Huntington Woods, MI (US)

(72) Inventors: Albert E. Sanders, San Antonio, TX (US); James O. Sanders, Pittsford, NY (US); Ronald G. Blackman, Oakland, CA (US); Robert B. More, Austin, TX (US); Brian Snyder, Westwood, MA (US); Grant D. Hogue, San Antonio, TX (US); Ira Zaltz, Huntington Woods, MI (US)

(73) Assignee: Tether Implant Corporation, San Antonio, TX (US)

( * ) Notice: Subject to any disclaimer, the term of this patent is extended or adjusted under 35 U.S.C. 154(b) by 0 days.

(21) Appl. No.: 16/411,831

(22) Filed: May 14, 2019

Related U.S. Application Data

(60) Provisional application No. 62/728,062, filed on Sep. 6, 2018, provisional application No. 62/806,121, filed on Feb. 15, 2019.

(51) Int. Cl.
*A61B 17/70* (2006.01)
*A61B 17/80* (2006.01)

(52) U.S. Cl.
CPC ...... *A61B 17/7044* (2013.01); *A61B 17/7032* (2013.01); *A61B 17/7059* (2013.01); *A61B 17/809* (2013.01)

(58) Field of Classification Search
CPC ............ A61B 17/7044; A61B 17/7032; A61B 17/7059; A61B 17/809
USPC ....... 606/263, 267, 270, 271, 286, 297, 301, 606/305, 308, 328, 329
See application file for complete search history.

(56) References Cited

U.S. PATENT DOCUMENTS

| | | | | |
|---|---|---|---|---|
| 4,793,335 A * | 12/1988 | Frey | .................. | A61B 17/0642 411/457 |
| 5,314,427 A * | 5/1994 | Goble | ................ | A61B 17/0642 411/457 |
| 5,620,443 A * | 4/1997 | Gertzbein | .......... | A61B 17/7041 606/250 |
| 5,899,905 A * | 5/1999 | Errico | ................ | A61B 17/7032 606/256 |
| 5,947,969 A * | 9/1999 | Errico | ................ | A61B 17/7044 606/308 |
| 6,325,805 B1 * | 12/2001 | Ogilvie | .............. | A61B 17/0642 606/300 |
| 9,119,676 B2 * | 9/2015 | Daly | .................. | A61B 17/7032 |

(Continued)

*Primary Examiner* — Pedro Philogene
*Assistant Examiner* — David C Comstock
(74) *Attorney, Agent, or Firm* — Conley Rose, P.C.

(57) ABSTRACT

Embodiments disclosed herein include systems for the treatment of spinal deformity in children by harnessing growth modulation without requiring vertebral fusion. In some embodiments, the system uses flexible or moveable elements to selectively apply and tune forces and moments to the spine instead of rigid fixation and vertebral segment fusion.

19 Claims, 9 Drawing Sheets

(56) References Cited

U.S. PATENT DOCUMENTS

| | | | |
|---|---|---|---|
| 2002/0068940 A1* | 6/2002 | Gaines, Jr. ......... | A61B 17/7044 |
| | | | 606/75 |
| 2004/0162558 A1* | 8/2004 | Hegde ................ | A61B 17/7044 |
| | | | 606/287 |
| 2006/0217715 A1* | 9/2006 | Serhan ................ | A61B 17/0642 |
| | | | 606/86 A |
| 2010/0094358 A1* | 4/2010 | Moore ............... | A61B 17/0642 |
| | | | 606/319 |
| 2014/0066991 A1* | 3/2014 | Marik ................ | A61B 17/7032 |
| | | | 606/279 |

* cited by examiner

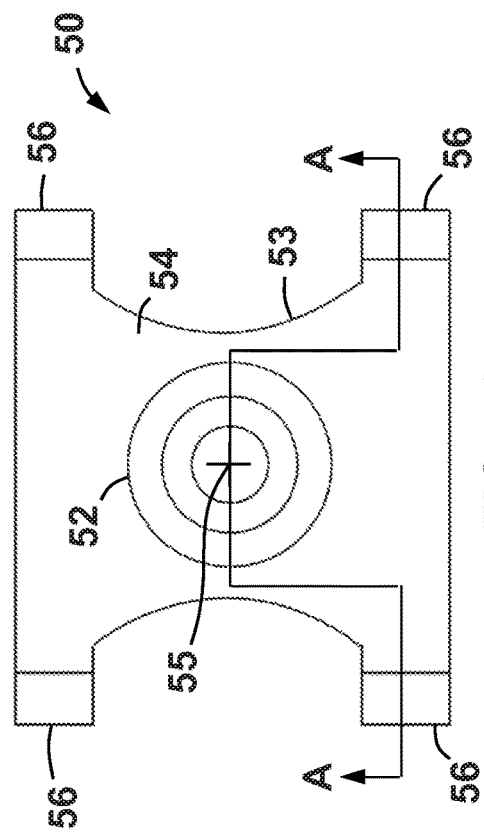
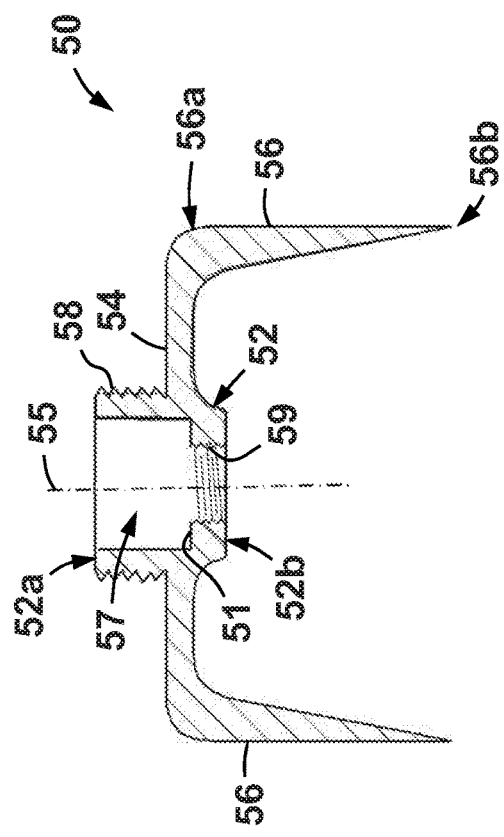
FIG. 5A
FIG. 5B

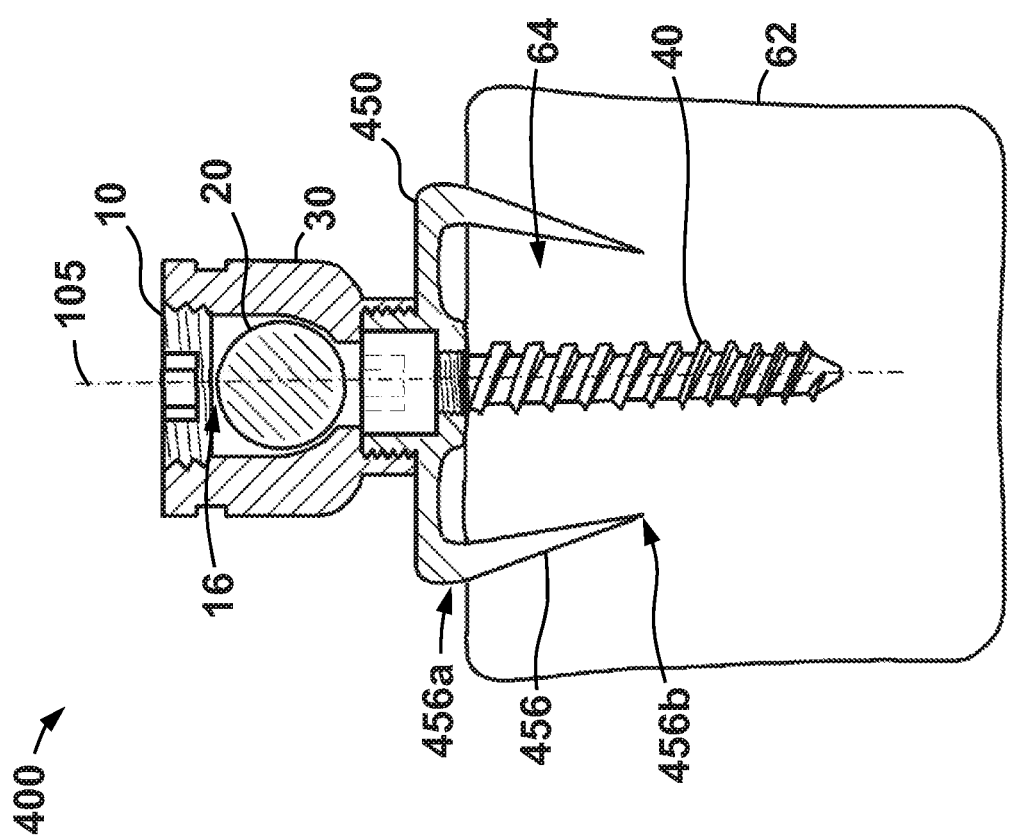

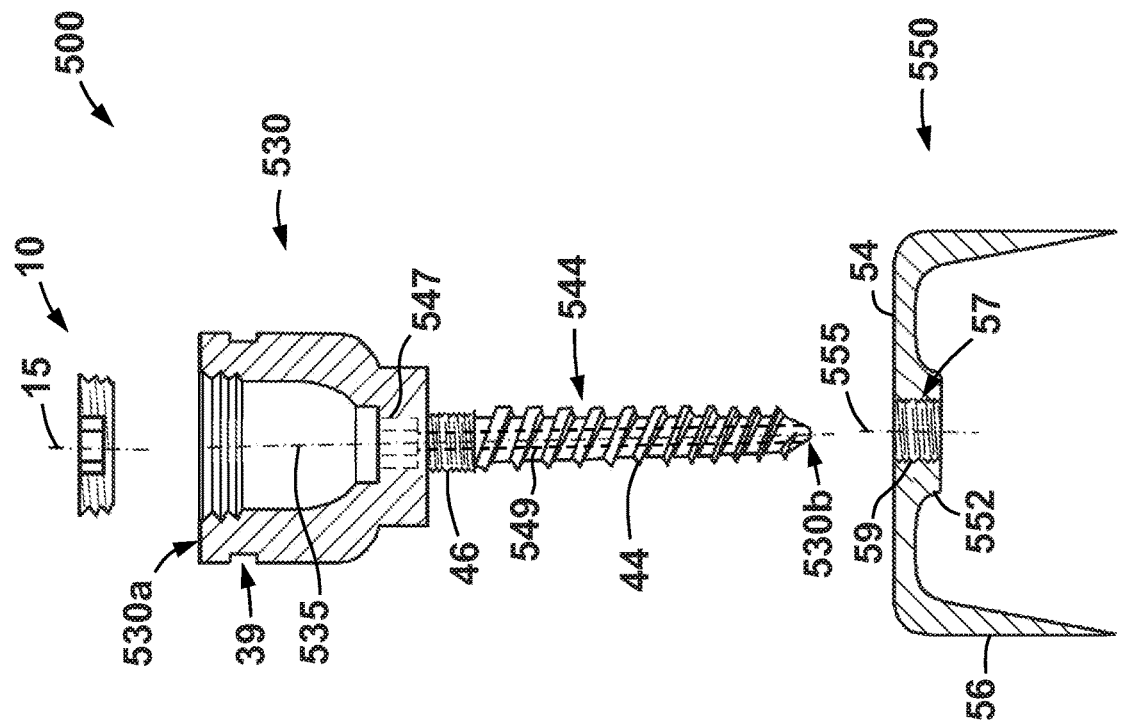
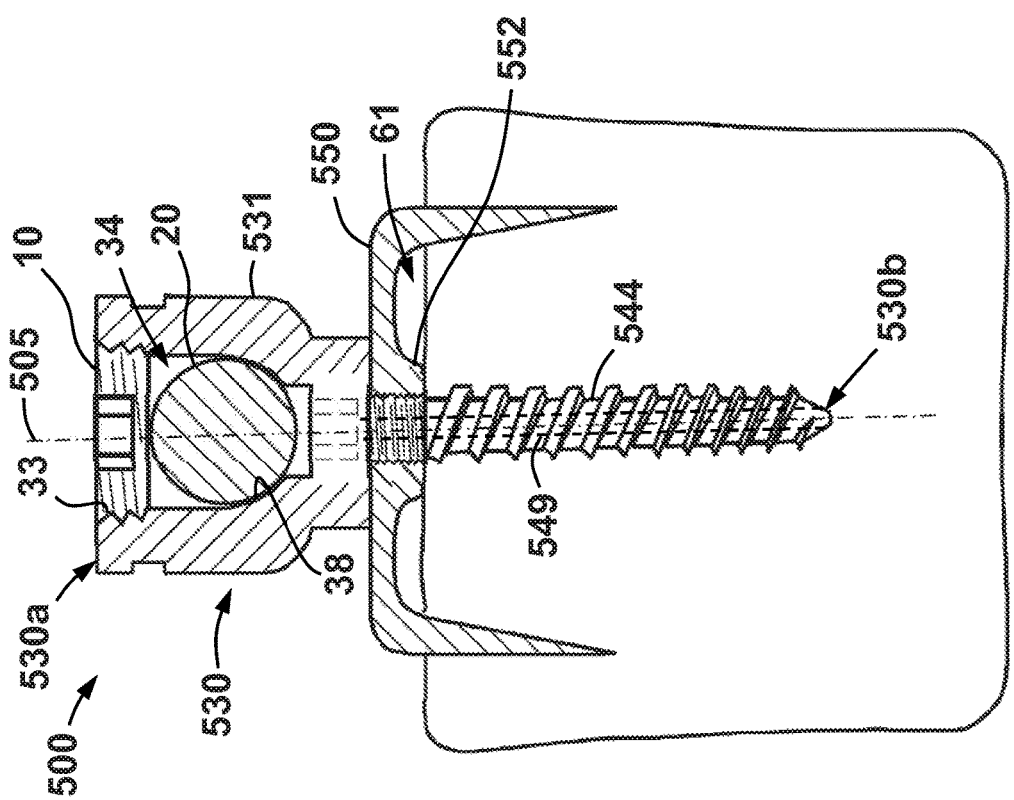

SYSTEMS FOR TREATMENT OF SPINAL DEFORMITIES

CROSS-REFERENCE TO RELATED APPLICATIONS

This application claims benefit of U.S. provisional patent application Ser. No. 62/728,062 filed Sep. 6, 2018, and entitled "SYSTEMS FOR TREATMENT OF SPINAL DEFORMITIES" and U.S. provisional patent application Ser. No. 62/806,121 filed Feb. 15, 2019, and entitled "SYSTEMS FOR TREATMENT OF SPINAL DEFORMITIES" which are hereby incorporated herein by reference in their entireties.

STATEMENT REGARDING FEDERALLY SPONSORED RESEARCH OR DEVELOPMENT

Not applicable.

BACKGROUND

This disclosure relates generally to the treatment of spinal deformities. More particularly, the disclosure relates to implantable systems for the treatment of spinal deformities. Implant systems for the surgical correction of spinal deformities typically employ rigid vertebral fixation to support segmental fusion between one or more vertebrae in order to correct deformity. However, rigid fixation and segmental fusion are typically not used in a rapidly growing child; therefore surgical correction is typically postponed until early adolescence when rapid growth subsides.

BRIEF SUMMARY

Some embodiments disclosed herein are directed to an anchor for a spinal implant system. In an embodiment, the anchor includes a central axis, a base including a plurality of struts, and a head that is configured to be coupled to the base. The head includes a radially extending slot configured to receive an elongate connector therethrough. In addition, the anchor includes an axially extending threaded portion including a first thread configured to engage within a spinal vertebrae to mount the base and the head to the spinal vertebrae.

Other embodiments disclosed herein are directed to a spinal implant system for treating a spinal deformity. In an embodiment, the system includes an elongate connector, and a plurality of anchors configured to be coupled to the elongate connector. Each of the plurality of anchors is configured to be mounted to a corresponding vertebrae of a spine. Each of the plurality of the anchors includes a central axis, a base including a plurality of struts, and a head that is configured to be coupled to the base. The head includes a radially extending slot configured to receive the elongate connector therethrough. In addition, each of the plurality of anchors includes an axially extending threaded portion including a first thread configured to engage within a spinal vertebrae to mount the base and the head to the spinal vertebrae.

Still other embodiments disclosed herein are directed to a spinal implant system for treating a spinal deformity. In an embodiment, the system includes an elongate connector and a plurality of anchors coupled to the elongate connector. Each of the plurality of anchors is configured to be secured to a corresponding spinal vertebrae. Each of the plurality of anchors includes a longitudinal axis and a head including a slot that extends radially through the head with respect to the longitudinal axis. The plurality of anchors include a pair of external anchors, and a set of internal anchors disposed between the external anchors along the elongate connector. The elongate connector is fixed within the slot of each of the external anchors and is movable within the slot of each of the internal anchors.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a detailed description of various exemplary embodiments, reference will now be made to the accompanying drawings in which:

FIG. 5A is a top view of a base of the anchor of FIGS. 2 and 3;

FIG. 5B is a cross-sectional view taken along section A-A in FIG. 5A;

FIG. 6 is a cross-sectional view of another anchor for use within the system of FIG. 1 according to some embodiments;

FIG. 7 is a cross-sectional view of another anchor for use within the system of FIG. 1, according to some embodiments;

FIG. 8 is an exploded assembly view of the anchor of FIG. 7;

DETAILED DESCRIPTION

Figure 1:
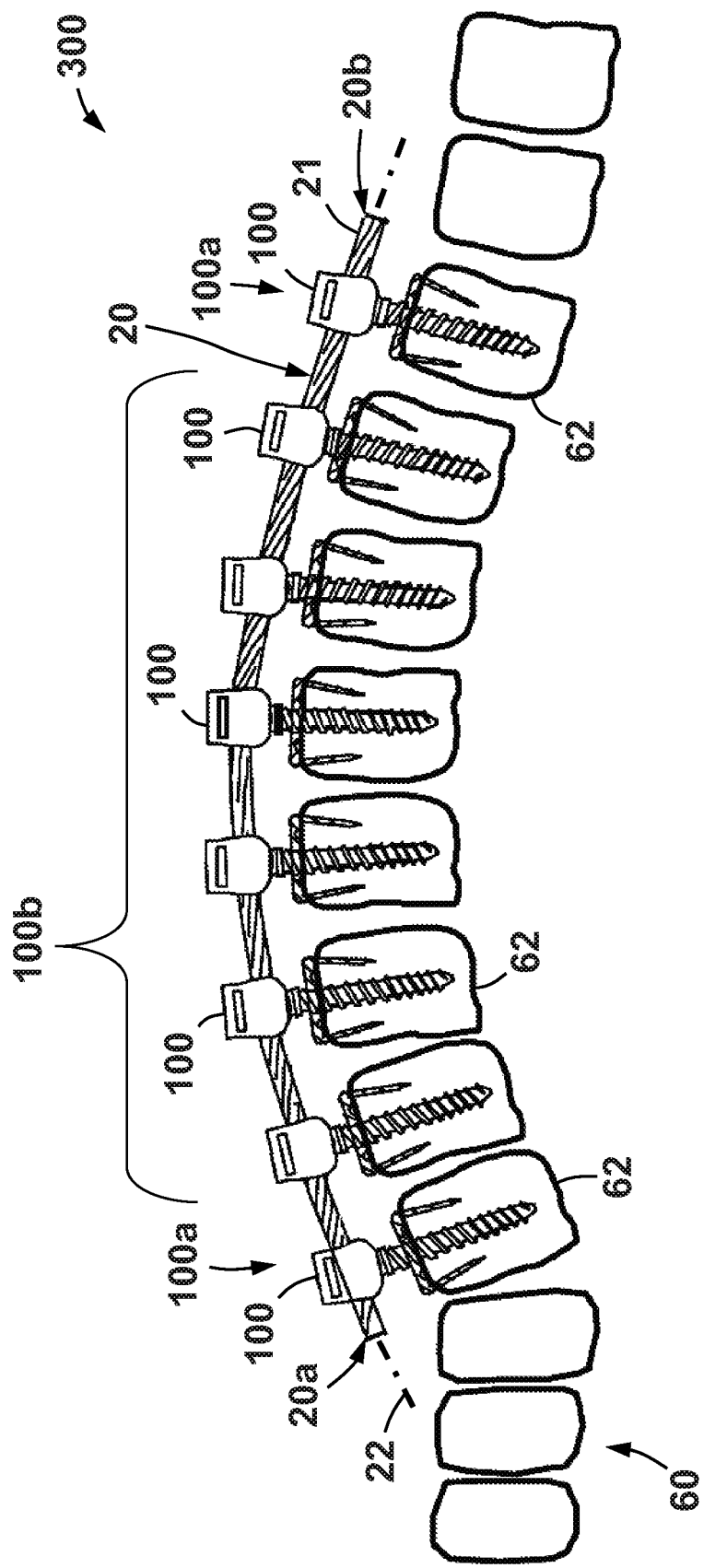
FIG. 1 is a side view of a spinal implant system for correcting spinal deformities, according to some embodiments.

The following discussion is directed to various exemplary embodiments. However, one of ordinary skill in the art will understand that the examples disclosed herein have broad application, and that the discussion of any embodiment is meant only to be exemplary of that embodiment, and not intended to suggest that the scope of the disclosure, including the claims, is limited to that embodiment.

The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection of the two devices, or through an indirect connection that is established via other devices, components, nodes, and connections. In addition, as used herein, the terms "axial" and "axially" generally mean along or parallel to a given axis (e.g., central axis of a body or a port), while the terms "radial" and "radially" generally mean perpendicular to the given axis. For instance, an axial distance refers to a distance measured along or parallel to the axis, and a radial distance means a distance measured perpendicular to the axis.

As previously described above, rigid vertebral fixation and segmental fusion are typically not used to correct spinal deformities in rapidly growing children. In particular, rapid post-surgical growth of the spine may cause or lead to a multitude of post-surgical complications following such a procedure. Accordingly, embodiments disclosed herein include systems and methods for correcting spinal deformities that are configured to apply selectively biased loads and moments to the convex curve of a spine. Without being limited to any particular theory, the selectively applied loads and moments may harness the natural growth of the patient's spine to promote a greater relative longitudinal growth on the concave side of the spine, and thereby correct spinal curvature deformities without column support, rigid fixation, or vertebral segment fusion.

Referring now to FIG. 1, an embodiment of a spinal implant system 300 for correcting spinal deformities is shown. More particularly, FIG. 1 shows system 300 disposed along the anterior side of the spine 60 of a patient (not shown). In this embodiment, the system 300 is shown mounted to a curved thoracic segment (i.e., a rib cage portion) of spine 60; however, it should be appreciated that the system 300 may be attached to any vertebral section in other embodiments. Generally speaking, system 300 comprises an elongate connector 20 (which may also be referred to herein as a "longitudinal force element"), and a plurality of anchors 100 coupled to elongate connector 20 that are each secured to a corresponding vertebrae 62 of spine 60. More specifically, the plurality of anchors 100 includes a pair of first or outer anchors 100*a*, and a plurality of second or inner anchors 100*b* disposed between the outer anchors 100*a* along the elongate connector 20.

Referring still to FIG. 1, elongate connector 20 includes a longitudinal axis 22, a first end 20*a*, a second end 20*b* opposite first end 20*a*, and an external surface 21 extending between ends 20*a*, 20*b*. In this embodiment, elongate connector 20 is an elongate cable that may be elastically and/or plastically deformed or curved. As a result, longitudinal axis 22 may be curved during operations such as generally shown in FIG. 1. In addition, elongate connector 20 may retain a sufficient amount of rigidity to resist (at least somewhat) an imposed deformation or curvature, to thereby generate reactionary forces (which may be transferred to anchors 100 and thus spine 60, as will be described in more detail below). Elongate connector 20 may comprise any suitable material (e.g., metal, polymer, composite, etc.) to provide the functionality described herein. For example, in some embodiments, connector 20 comprises a shape memory alloy, such as, Nickel Titanium (e.g., Nitinol), polyester tape, stranded polymer cable, titanium cable, titanium alloy, titanium cable, carbon fiber, reinforced polyether ether ketone (PEEK).

Also, in this embodiment, elongate connector 20 has a circular cross-section. However, as will be described in more detail below, the cross-section of elongate connector 20 may have any suitable shape in other embodiments, such as, for example, elliptical, square, rectangular, triangular, polygonal, D-shaped, etc.

Figure 2:
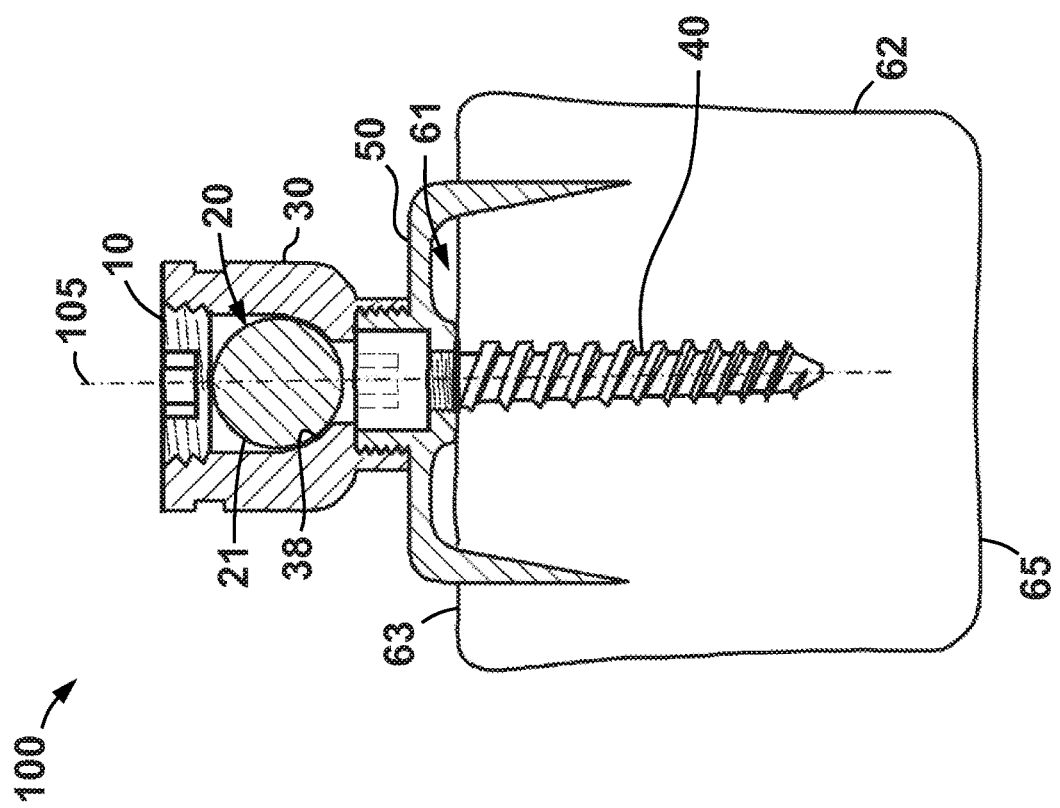
FIG. 2 is a cross-sectional view of an anchor of the system of FIG. 1 inserted within a vertebrae, according to some embodiments.

Referring now to FIGS. 1 and 2, each of the anchors 100 (including outer anchors 100*a* and inner anchors 100*b*) comprises an axis 105, a setscrew 10, a head 30, a screw 40, and a base 50. As best shown in FIG. 1, during operations, each anchor 100 is coupled to elongate connector 20 so that axis 105 is generally orthogonal (or perpendicular) to longitudinal axis 22 at the corresponding position along connector 20. In addition, as best shown in FIG. 2, in some embodiments, each anchor 100 is secured to a corresponding vertebrae 62 such that axis 105 extends in a normal direction relative to a first cortex surface 63 of the corresponding vertebrae 62. However, it should be appreciated that such precise alignment is not achieved (and indeed may not be desirable) in other embodiments. For example, adjustments to the angle of axis 105 relative to vertebra 62 may be made based on a multitude of factors, including patient anatomy, surgical access (or the limit thereof), and the desired amount of force correction imparted to spine 60 by system 300.

Figure 3:
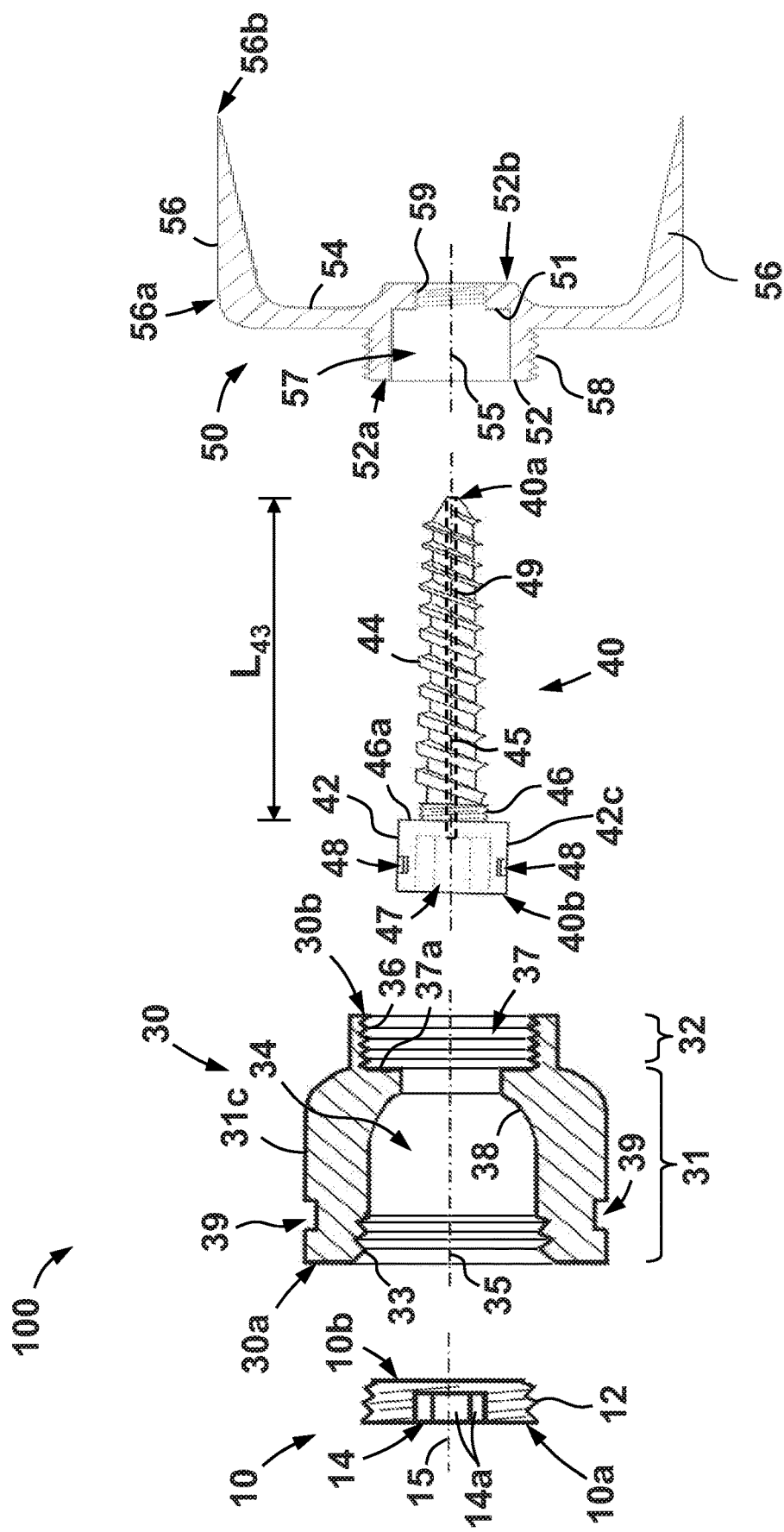
FIG. 3 is an exploded assembly view of the anchor of FIG. 2.

Referring now to FIGS. 2 and 3, set screw 10 is a generally cylindrical and includes a central or longitudinal axis 15 that is aligned with (or coincides with) axis 105 of anchor 100, during operations. In addition, set screw 10 includes a first end 10*a*, a second end 10*b* opposite first end 10*a*, a recess 14 extending axially from first end 10*a*, and an external thread 12 extending between ends 10*a*, 10*b*. In this embodiment, recess 14 includes a plurality of axially extending planar surfaces 14*a*, which engage and mate with corresponding planar surfaces on a suitable tool (not shown) as described in more detail below.

Head 30 includes a central or longitudinal axis 35 that is aligned with (or coincides with) axis 105 of anchor 100, during operations. In addition, head 30 comprises a first end 30*a*, a second end 30*b* opposite the first end 30*a* along central axis 35, a first portion 31 extending axially from first end 30*a*, and a second portion 32 extending axially from first portion 31 to second end 30*b*.

First portion 31 includes open slot 34 extending axially from first end 30*a* and radially through first portion 31 across axis 35. In addition, second portion 32 includes bore 37 extending axially from slot 34 to second end 30*b*. Slot 34 includes an internal thread 33 extending from first end 30*a*, and bore 37 includes a second internal thread 36 extending from second end 30*b*. Slot 34 includes a seat 38 defined therein that is to engage with external surface 21 of elongate connector 20 during operations (see FIG. 2). Because elongate connector 20 has a circular cross-section in this embodiment as previously described above, seat 38 is generally arcuate in shape in order to facilitate engagement between seat 38 and external surface 21 of connector 20 during operations. Bore 37 includes a radially extending annular shoulder 37*a* that, as will be described in more detail below, engages or abuts with base 50 during operations.

Referring still to FIGS. 2 and 3, a plurality of recesses 39 extend radially inward toward axis 35 from an outer surface 31*c* of first portion 31. In this embodiment, there are a total of two recesses 39 that are radially opposite one another across axis 35; however, it should be appreciated that the number and arrangement of recesses 39 may be altered in other embodiments. As will be described in more detail below, recess 39 are configured to be engaged by an appropriate tool (not shown) so that a user may apply toque to head 30 about axis 35 during operations.

Figures 4A, 4B:
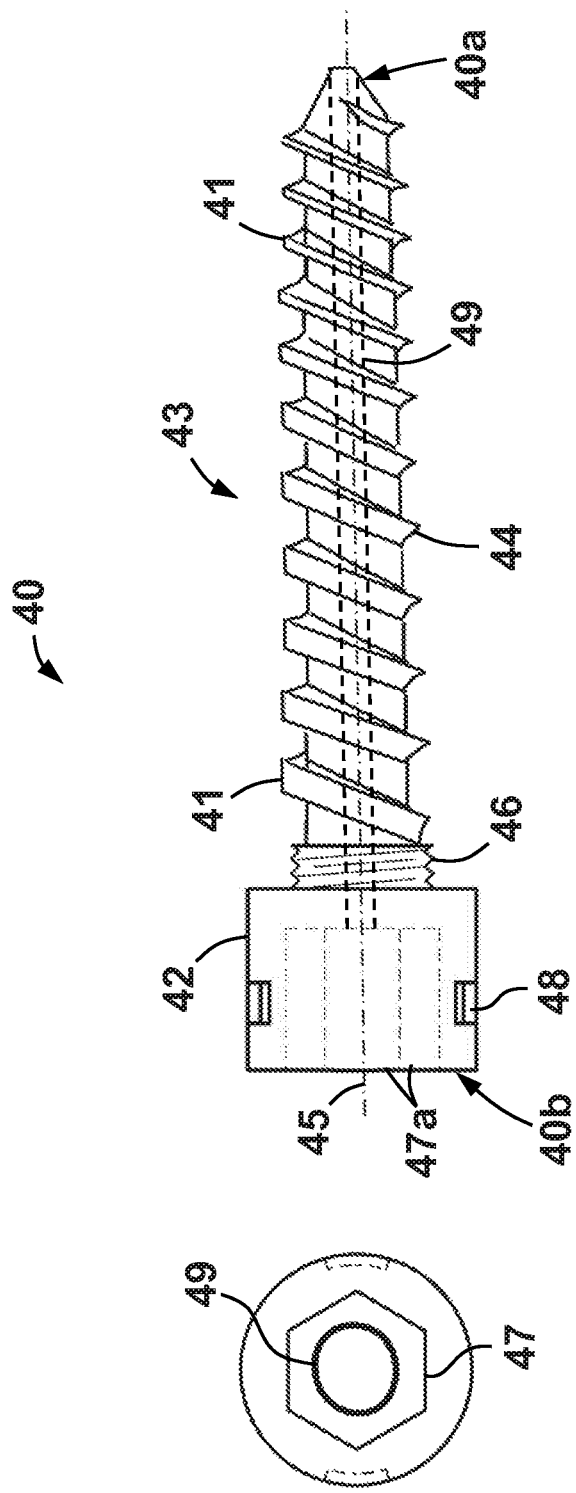
FIGS. 4A and 4B are top and side views, respectively, of the screw of the anchor of FIGS. 2 and 3.

Referring now to FIGS. 3, 4A, and 4B, screw 40 comprises a central or longitudinal axis 45 that is aligned with (or coincides with) axis 105 of anchor 100, during operations. In addition, screw 40 comprises a first end 40a, a second end 40b opposite the first end 40a, a cylindrical screw head 42 at the second end 40b, and a threaded portion 43 extending axially from screw head 42 to first end 40a.

Threaded portion 43 includes a first thread 44 extending axially from first end 40a, and a second thread 46 extending axially from first thread 44 to screw head 42. The first thread 44 is different from the second thread 46. In particular, as will be described in more detail below, second thread 46 is configured to threadably engage with a corresponding thread on base 50, whereas first thread 44 is configured to engage within a corresponding vertebrae (e.g., vertebra 62) during operations. Second thread 46 is shown in this embodiment as straight threads. However, in other embodiments, second thread 46 may include a number of different types or shapes of threads. For example, in some embodiments, second thread 46 may include tapered or locking threads.

In addition, the pitch and other thread characteristics of first thread 44 can be varied as needed to provide various insertion and cortical wall fixation benefits. For example, in some embodiments, first thread 44 may include a variable pitch, progressive thickening of the thread lands or thread profile when moving along the axial direction, self-tapping or thread cutting tips, axially oriented slots, or a combination thereof. In particular, as best shown in FIG. 4B, in this embodiment, first thread 44 includes a thread land or crest 41 that generally increases in axial width when moving axially from the first end 40a toward second end 40b. Without being limited to this or any other theory, the increasing axial width of land 41 within first thread 44 provides a thread engagement that tends to tighten as it is installed into the corresponding vertebrae 62 (e.g., due to increasing friction). The gradual increase in friction during axial advance of the screw 40 may provide tactile feedback to the clinician, in the form of increasing torque, which may be helpful from an ergonomics perspective and may also contribute to enhanced fixation within vertebrae 62 as a relatively greater torque will be required to disengage screw 40 from vertebrae 62 following installation. Moreover, in this embodiment, the pitch of thread 44 is maintained constant (or substantially constant) between second thread 46 and first end 40a; however, in other embodiment, a variable (e.g., increasing, decreasing, or combination thereof) may be employed within first thread 44. Additionally, thread 44 may include multiple leads or include a minor thread diameter that increases along the length of first thread 44 when moving axially from the first end 40a toward second end 40b.

Screw head 42 includes a drive recess 47 that extends axially from second end 40b. Drive recess 47 includes a plurality of axially extending planar surfaces 47a that mate with corresponding planar surfaces on a suitable tool (not shown) as described in more detail below. The arrangement of planar surfaces 47a within drive recess 47 may correspond to any cross-sectional profile as desired to mate with a suitable tool (e.g., driver), such as, for example, torx, hexalobe, allen drive, etc. A radially extending annular shoulder 46a is defined on screw head 42 axially adjacent second thread 46. In addition, a plurality of recesses 48 extend radially inward toward axis 45 from an outer surface 42c of screw head 42. In this embodiment, there are a total of two recesses 48 that are radially opposite one another across axis 45; however, it should be appreciated that the number and arrangement of recesses 45 may be altered in other embodiments. In some embodiments, recesses 48 are engaged by an appropriate tool (e.g., a spanner wrench) to apply torque to screw head 42, so as to urge rotation of screw 40 about axis 45 or to resist and counteract such rotation. In some embodiments, the recesses 48 are interconnected, such as, for example, by cross drilling a thru hole fully through screw head 42 in a radial direction.

As best shown in FIG. 3, the threaded portion 43 of screw 40 has a total length $L_{43}$ measured axially between screw head 42 and first end 40a with respect to axis 45. In at least some embodiments, the length $L_{43}$ is set based on patient anatomy. For example, in some embodiments, $L_{43}$ may be set such that both the first cortex surface and the second, opposing cortex surface of a corresponding vertebrae (e.g., surfaces 63 and 65, respectively, of vertebrae 62 shown in FIG. 2) are interfaced (bicortical) by screw 40. In other embodiments, length $L_{43}$ may be set such that only a single cortical surface of the corresponding vertebrae (e.g., first cortex surface 63 vertebrae 62) is interfaced (unicortical).

Referring still to FIGS. 3, 4A, 4B, in this embodiment, screw 40 also includes a throughbore or cannula 49 that extends axially from drive recess 47 to first end 40a. Cannula 49 is configured to provide access for an elongate guide member (e.g., a guide wire or pin, such as a K-wire or Steinmann pin, etc.) to be used during the placement of anchors 100. It should be appreciated that screw 40 may not include cannula 49 in other embodiments.

Referring now to FIGS. 3, 5A, and 5B, base 50 comprises a central or longitudinal axis 55 that is aligned with (or coincides with) axis 105 of anchor 100, during operations. In addition, base 50 comprises a central hub 52 extending along axis 55, a radial plate 54 extending radially outward from central hub 52 relative to central axis 55, and a plurality of struts or lateral outrigger legs 56 extending from radial plate 54.

Central hub 52 is a generally cylindrical member that includes a first end 52a, a second end 52b opposite first end 52a, and a through passage 57 extending between ends 52a and 52b. An external thread 58 extends from first end 52a. In addition, through passage 57 includes a radially extending annular shoulder 51, and an internal thread 59 extending from annular shoulder 51 to second end 52b. As will be described in more detail below, external thread 58 is configured to threadably engage with internal thread 36 on head 30, and internal thread 59 is configured to threadably engage with second thread 46 on screw 40 during operations.

Referring still to FIGS. 3, 5A, and 5B radial plate 54 surrounds central hub 52 and extends radially outward therefrom with respect to axis 55 at a point between ends 52a, 52b. Thus, radial plate 54 is axially spaced from first end 52a and second end 52b. Radial plate 54 includes an outer perimeter or periphery 53 that may have any suitable shape when viewed axially along axis 55 (see e.g., FIG. 5A). For example, perimeter 53 may, in other embodiments, be rectangular, triangular, circular, oval, etc.

The plurality of struts 56 are disposed about perimeter 53 and extend generally axially therefrom with respect to axis 55. In this embodiment, there are a total of four struts evenly spaced about axis 55; however, other arrangements and quantities are possible for struts 56 in other embodiments. For example, some embodiments of base 50 may include more or less than four struts, such as three, or five. In this embodiment, the generally even spacing of struts 56 about central axis 55 allows for balanced and relatively even load sharing amongst the struts 56 during operation. However, it should be appreciated that other embodiments may not include even spacing for struts 56. For example, in some embodiments struts 56 may be positioned unequal or at uneven distances about central axis 55, so that enhanced stability is achieved for certain desired orientations of base 50 or anchor 100 more generally. In particular, in the embodiment shown in FIG. 4B, if the one more of the struts 56 were positioned radially away from central axis 55 relative to the other struts 56, the bending resistance of base 50 would generally be increased along the translation direction so that greater forces and moments could then be applied to vertebrae 62 along this direction. Thus, within system 300 (see FIG. 1), bases 50 of anchors 100 may include a variety of different shapes and arrangements (particularly with respect to the shape and size of radial plate 54 and the arrangement and number of struts 56). As a result, in some embodiments, clinicians may tailor the specifics of each anchor 100 within system 300 (see FIG. 1) to match the magnitude of loads needed at each vertebrae installation position.

Each strut 56 includes a first or proximal end 56a that is mounted to radial plate 54 and a second or distal end 56b. Each Strut 56 generally tapers from proximal end 56a toward distal end 56b so that distal end 56b comprises a point, which allows strut 56 to penetrate into the cortex of a vertebrae (e.g., first cortex surface 63 of vertebrae 62). Struts 56 may be formed in a numerous number of shapes or profiles, some of which may be configured to enhance fixation within the corresponding vertebrae (e.g., vertebrae 62). In some instances struts 56 may include a relatively thin section to facilitate an enhanced penetration into first cortex surface 63 of the corresponding vertebrae 62 during operations. In addition, such thin sections may be spring loaded such that elastic deformations of the struts 56 may aid in their retention and stability. Struts 56 may comprise a shape memory alloys such as Nickle Titanium (e.g., Nitinol), in some embodiments, to provide a large elastic range and to allow for selective "spring loading" after installation (e.g., penetration) of the strut 56 within a corresponding vertebrae 62 (e.g., by using a heat source such as inductive heating, resistive heating, or body heat, or through a super-elasticity response.). In other embodiments, struts 56 may include a relatively thick sections to reduce deflections that may occur when strut 56 is mechanically loaded (e.g., by elongate connector 20). Also, thicker sections may provide stronger clamping forces between the "spring loaded" struts 56 and the vertebrae 62 during operations. In another embodiment, barbs or hooks may be disposed along the length of struts 56 (or at distal end 56b) to prevent or restrict the withdrawal of struts 56 from the corresponding vertebrae 62 during operations.

Referring still to FIGS. 3, 5A, and 5B, in this embodiment central hub 52, radial plate 54, and struts 56 of base 50 are integrated into a single, monolithic and continuous body. Thus, in some embodiments, the same material (e.g., a shape memory alloy and/or other metallic material) may be used to construct central hub 52, radial plate 54, and struts 56. However, it should be appreciated that in other embodiments, base 50 may not comprise a single, monolithic body and may instead comprise a number of different components or sections that are engaged or secured (e.g., threaded engagement, pinned engagement, etc.) to one another to form base 50.

Referring again to FIGS. 2 and 3, during operations in some embodiments, base 50 is installed onto first cortex surface 63 of a corresponding vertebrae 62 such that struts 56 penetrate into first cortex surface 63. First end 40a of screw 40 is then inserted through passage 57 of base 50 from first end 52a, so that axis 45 is aligned with axis 55. First end 40a engages with first cortex surface 63 of vertebrae 62 and screw 40 may be rotated (e.g., via a wrench or other tool that is engaged with axially extending planar surfaces 47a within drive recess 47) about axis 45 to thereby advance first end 40a of screw 40 into vertebrae 62 via engagement of first threads 44 on screw 40. In some embodiments, first end 40a may be advanced within a pilot hole formed in vertebrae 62 from first cortex surface 63. The advancement of screw 40 within vertebrae 62 may continue until second thread 46 engages with internal thread 59 on base 50 and/or annular shoulder 46a on screw head 42 engages or abuts with annular shoulder 51 within through passage 57 of base 50.

As previously described, in some embodiments, second thread 46 on screw 40 may include tapered or locking threads, such that multiple interface angles could be established between the axes 45, 55 of screw 40 and base 50, respectively. In other words, in these embodiments, the axis 45 of screw 40 may not be aligned with axis 55 of base 50, such that screw 40 may be referred to as a "polyaxial screw" in these embodiments. Allowing a skewed angle between screw 40 and the base 50 may provide easier installations of screw 40 during surgery as misalignments would less readily result in binding of second threads 46 with internal thread 59 on base 50. In some of these embodiments, cut reliefs of the screw second thread 46 and/or internal thread 59 on the base 50 may be included to provide increased angle variance between the axes 45, 55. Additionally, in these embodiments, screw head 42 may be modified in shape to provide adequate clearance with the base 50 to thereby provide firm and positive seating between the screw head 42 and base 50 (e.g., annular shoulder 46a and annular shoulder 51). For example, screw head 42 may have a hemispherical profile. Also, internal thread 59 may in some embodiments be provided as a smooth cylindrical bore such that no thread engagement occurs between screw 40 and base 50.

Thereafter, base 50 is threadably engaged with the head 30 via threaded engagement of internal threads 36 on head 30 and external threads 58 on central hub 52 of base 50. In particular, external threads 58 on central hub 52 of base 50 are engaged with internal threads 36 within bore 37 of head 30 so that first end 52a of central hub 52 is axially received within bore 37 along the aligned axes 35, 55. In this embodiment, the engagement of threads 36, 58 and axial advancement of first end 52a within bore 37 continues until first end 52a of central hub 52 engages or abuts with annular shoulder 37a formed within bore 37 of head 30 and/or second end 30b of head 30 engages or abuts with radial plate 54 on base 50.

Referring still to FIGS. 2 and 3, as anchor 100 is assembled and secured to vertebrae 62 as described above, a surgical instrument (e.g., a spanner wrench—not shown) may engage with recesses 39 to apply torque to rotate or resist rotation of head 30. In some embodiments, torque is applied to head 30 via recesses 39 to threadably engage head 30 with base 50 as previously described above. In other embodiments, torque may be applied to head 30 via recesses 39 to resist rotation of head 30 for example when set screw 10 is threadably engaged within slot 34. Also, the recesses 39 may indicate an angular alignment of head 30 (or anchor 100 more generally) during operations so that a particular alignment may be achieved. More specifically, the angular position of each anchor 100 is to be arranged such that elongate connector 20 may extend through the cavities 34 of each adjacent anchor 100, and the known positions of recesses 39 may be used to achieve the desired angular alignment between each of the cavities 34 during operations. In addition, the recesses 39 of anchors 100 (including both outer anchors 100a and inner anchors 100b) may be aligned such that surgical jigs or other similar instrumentation (e.g., to align cavities 34 of anchors 100 with the elongate connector 20 as described above) may be coupled to recesses 39.

Referring again to FIGS. 2 and 3, in some embodiments, when base 50 mates with vertebrae 62, vertical relief cavity 61 is formed therebetween. More specifically, as best shown in FIG. 2, because second end 52b of central hub 52 is axially spaced from radial plate 54 (e.g., with respect to axis 55, 105, etc.), when second end 52b of central hub 52 abuts or engages with first cortex surface 63 of vertebrae 62, radial plate 54 is spaced (e.g., axially spaced) from first cortex surface 63 such that relief cavity 61 is formed. In other words, relief cavity 61 is formed axially between radial plate 54 and first cortex surface 63 of vertebrae 62 along axis 105. This vertical relief cavity 61 provides clearance for the vertebral blood supply and relieves surface compression on vertebrae 62.

Referring now to FIGS. 1-3, each of the anchors 100 are mounted to corresponding adjacent vertebrae 62 of spine 60 in substantially the same manner as described above. Thereafter, elongate connector 20 is inserted within the slot 34 of each head 30 from first end 30a. During this process, external surface 21 of connector 20 may engage with the seat 38 in slot 34 of some or all of anchors 100. Subsequently, set screws 10 are threadably engaged within slot 34 of each head 30 to thereby retain or secure elongate connector 20 therein (e.g., see FIG. 2). In particular, for each anchor 100, external thread 12 on set screw 10 is threadably engaged with internal thread 33 within slot 34 of head 30 by rotating set screw 10 about the aligned axes 15, 35 (e.g., via a wrench or other tool that is engaged with axially extending planar surfaces 14a within recess 14) relative to head 30.

In this embodiment, elongate connector 20 is impinged or compressed within slot 34 of heads 30 of outer anchors 100a (see FIG. 1) so that elongate connector 20 may not move axially or rotationally relative to outer anchors 100a along axis 22. Conversely, elongate connector 20 is engaged within slot 34 of heads 30 of inner anchors 100b so that connector 20 may move axially and/or rotationally with respect to axis 22 relative thereto during and after operations. In particular, within outer anchors 100a, set screw 10 is threadably advanced within slot 34 until connector 20 is axially compressed between second end 10b of set screw 10 and seat 38 along aligned axes 15, 35, 105, etc. (i.e., until connector 20 is radially compressed between second end 10b and seat 38 along axis 22). Conversely, within inner anchors 100b, set screw 10 is not fully advanced within slot 34 so that there is clearance gap between connector 20 and seat 38 and/or second end 10b of set screw 10 (see e.g., clearance gap 16 shown in FIG. 6). Thus, following operations, compressive forces and moments from elongate connector 20 are applied to the inner anchors 100b, while reaction forces from elongate connector 20 act against outer anchors 100a, so that a relative positional straightening of the multiple vertebrae 62 is achieved. It should be appreciated that in some embodiments, one or more of the inner anchors 100b may also be secured to elongate connector 20 in the same manner as described above for outer anchors 100a.

In addition, in some embodiments, it may be desirable to prevent relative rotation of elongate connector 20 within heads 30 of inner anchors 100b, but still allow relative axial translation of elongate member 20 along axis 22 as described above relative to inner anchors 100b. In these embodiments, the cross-section of elongate connector 20 and/or the shape of seat 38 within slot 34 of heads 30 may be arranged so as to prevent such relative rotation about axis 22 (e.g., such as by providing elliptical, D-shaped, square, rectangular, triangular, polygonal, etc. shape for the cross-section of elongate connector 20 and/or seat 38).

Without being limited to this or any other theory, by allowing rotational and/or axial movement of elongate member 20 relative to inner anchors 100b, corrective loads are applied to vertebrae 62, yet the local angle between the elongate connector 20 and each of the plurality of inner anchors 100b remains flexible and adaptable to the newly corrected radius of curvature. The sliding engagement or translation of elongate connector 20 within slot 34 of inner anchors 100b allows the distance between each of the plurality of inner anchors 100b to remain adjustable to the newly corrected radius of curvature, so as to maintain proper spacing between individual vertebrae 62. Larger radiuses of curvature result in a larger arc length along the elongate connector 20, and thus if inner anchors 100b were axially fixed to elongate connector 20 (e.g. such as is described above for outer anchors 100a) the vertebrae 62 engaged with inner anchors 100b may be spread apart as spine 60 is straightened. Accordingly, the selective fixation between anchors 100 and elongate connector 20 (e.g., by selectively tightening set screws 10 as previously described) allows a clinician to target local deformities while concurrently accommodating the vertebrae 62 spacing of the surrounding spine 60.

Referring still to FIGS. 1-3, in some embodiments, slot 34 of inner anchors 100b (e.g., particular seat 38) includes a friction reducing coating (e.g., a ceramic) that is configured to reduce the coefficient of friction between slot 34 (particularly seat 38) and elongate connector 20 to provide enhanced sliding engagement therebetween. In addition, in some embodiments the friction reducing coating may also reduce the wear between elongate connector 20 and slot 34 of inner anchors 100b, reduce material galling, and/or may electrically insulate (or even isolate) anchors 100 to reduce galvanic corrosion therebetween.

Once anchors 100 (including outer anchors 100a and inner anchors 100b) are secured to vertebrae 62 of spine 60 and elongate connector 20 is secured to anchors 100 in the manner described above, the connector 20 and anchors 100 may transmit forces to vertebrae 62, in order to correct a deformity in spine 60. During operations, elongate connector 20 may be placed in a number of different profiles (e.g., straight and curved, or a combination thereof) to impart desired and targeted loads to specific vertebrae 62. More particularly, the shape or profile of elongate connector 20 is arranged to provide a desired force (e.g., including both a desired direction and magnitude) to each vertebrae 62 so as to correct a given patient's specific spinal deformity.

In embodiments where elongate connector 20 is constructed wholly or partially from a shape memory alloy (e.g., Nitinol as described above) as described above, control of the shape memory recovery of the elongate connector 20 after surgical installation can result in additional forces being exerted on anchors 100, and thus vertebrae 62 of spine 60. In particular, during these post-surgical operations, positionally selective and/or incremental heating of elongate connector 20 is possible by a clinician using, for example, an inductive heater. As a result, it is possible to apply post-surgical adjustments in the curvature correction provided by system 300.

In the embodiment of FIGS. 2 and 3, the struts 56 extend generally axially relative to axis 55 of base 50 as previously described above; however, in other embodiments, one or more of the struts 56 may be biased (or spring loaded) in a radial direction with respect to axis 55. For example, referring now to FIG. 6, another anchor 400 for use within system 300 in place of outer anchors 100a and/or inner anchors 100b is shown. Anchor 400 is generally the same as anchors 100 previously described above, and thus, features of anchor 400 that are shared with anchor 100 are identified with the same reference numerals, and the discussion below will focus on the features of anchor 400 that are different from anchors 100. In particular, in this embodiment, anchor 400 includes a base 450 that includes a plurality of struts 456 in place of struts 56 (otherwise, base 450 is the same as base 50 as previously described above). Struts 456 are generally similar as struts 56, except that struts 456 have a distal end 456b that is biased or "spring loaded" inward toward a plane containing axis 55 (and thus also axes 105, 10, 35, 45, etc.) relative to its proximal end 456a. As a result, once struts 456 are embedded or inserted within vertebrae 62, the inward bias of distal ends 456b of struts 456 results in a compression of a captured region 64 within vertebrae 62. It should be appreciated that the deflection or biasing of distal end 456b of each strut 56 is exaggerated in FIG. 6 to more clearly depict the compressive loads applied to captured region 64 during operations. Without being limited to this or any other theory, compression of captured region 64 within vertebrae 62 may enhance the engagement between anchor 400 and vertebrae 62 and therefore better facilitate the transfer of corrective forces into vertebrae 62 during operations.

In some embodiments, the bias or "spring loading" provided by struts 456 may be achieved by constructing struts 456 (e.g., either wholly or partially) from a shape memory alloy, such that post installation heating (e.g., inductive heating) of struts 456 may impart the desired bias thereto. In other embodiments, the above described "spring loaded" fit provided by struts 456 may be achieved by elastically deforming the struts 456 and/or base 450 during installation (e.g., using a suitable installation tool), and then releasing or removing the elastic deformation placed on the strut 456 and/or base 450 so that the biased strut 456 imparts the compressive loads to vertebrae 62 (e.g., to captured region 64) as previously described above. In addition, it should also be appreciated that struts 456 may alternatively be biased generally outward from a plane containing the axis 55 (rather than inward as shown in FIG. 6) in some embodiments.

Figure 9:
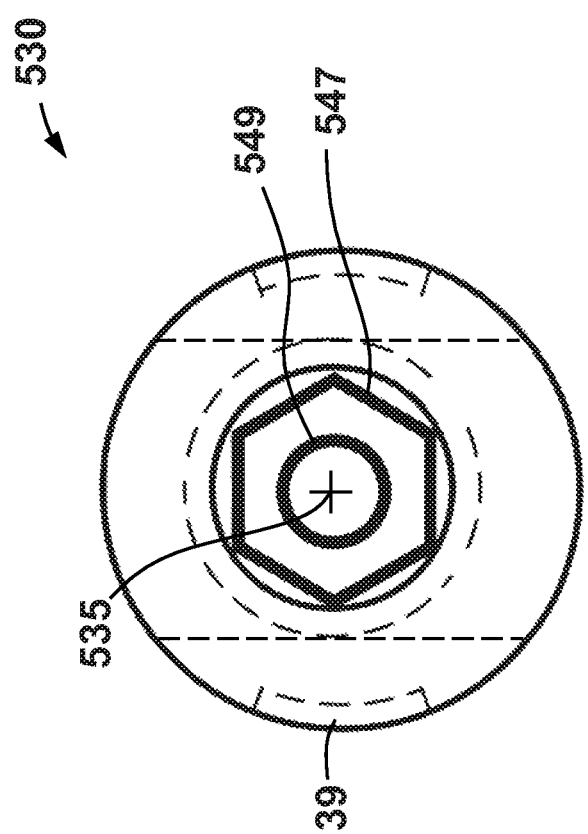
FIG. 9 is a top view of the head of the anchor of FIG. 8.

Referring now to FIGS. 7-9, another anchor 500 is illustrated that may be used within system 300 (see FIG. 1) in place of some or all of anchors 100 previously described above. Generally speaking, anchor 500 is similar to anchor 100 previously described, and thus, components of anchor 500 that are shared with anchor 100 are identified with like reference numerals, and the description below will focus on features of anchor 500 that are different from anchor 100. In particular, anchor 500 includes a central axis 505, set screw 10, a head assembly 530, and a base 550.

Head assembly 530 is a monolithic unibody design that is used in place of the separate head 30 and screw 40 of anchor 100 (see FIGS. 2 and 3). In particular, head assembly 530 includes a central axis 535 that is aligned (or is coincident) with central axis 505 of anchor 500 during operations, a first end 530a, and a second end 530b opposite first end 530a. In addition, head assembly 530 includes a head portion 531 extending from first end 530a, and a threaded portion 544 extending axially from head portion 531 to second end 530b.

Head portion 531 may be generally the same as head 30 previously described above (see FIGS. 2 and 3). In particular, head portion 531 includes recesses 39 and open slot 34 as previously described above for head 30. However, in place of bore 37, head portion 531 includes drive recess 547 extending axially from a terminal end of slot 34 toward second end 530b. Drive recess 547 is generally the same as drive recess 47 for screw 40, previously described, and thus, such description is not repeated in the interests of brevity.

Referring still to FIGS. 7-9, threaded portion 544 is generally the same as the threaded portion 43 of screw 40 (see FIGS. 3, 4A, and 4B), and thus includes first thread 44 and second thread 46 as previously described above. In addition, as with screw 40, threaded portion 544 of head assembly 530 includes a central throughbore or cannula 549 extending axially from drive recess 547 to second end 530b. During operations, cannula 549 may receive a guide wire or pin therethrough in the same manner as described above for screw 40. It should be appreciated that other embodiments of head assembly 530 may not include cannula 549.

Base 550 includes axis 555 that is aligned (or is coincident) with central axis 505 of anchor 500 during operations. Generally speaking, base 550 includes central hub 552, radial plate 54, and struts 56, wherein radial plate 54 and struts 56 are the same as described above for base 50. In addition, central hub 552 is generally the same as central hub 52, but central hub 552 does not include external thread 58 (see FIGS. 3 and 5B) and internal thread 59 extends throughout through passage 57.

Operations with anchor 500 are generally the same as those described above for anchor 100. However, rather than separately engaging head 30 with base 50, the monolithic head assembly 530 is inserted through passage 57 of base 550 to thereby threadably engage first thread 44 with vertebrae 62 and second thread 46 with internal thread 59. During these operations, a clinician may rotate head assembly 530 relative to base 550 by engaging an appropriate tool (e.g., a wrench—not shown) with drive recess 547 and/or with recesses 39.

Figure 10:
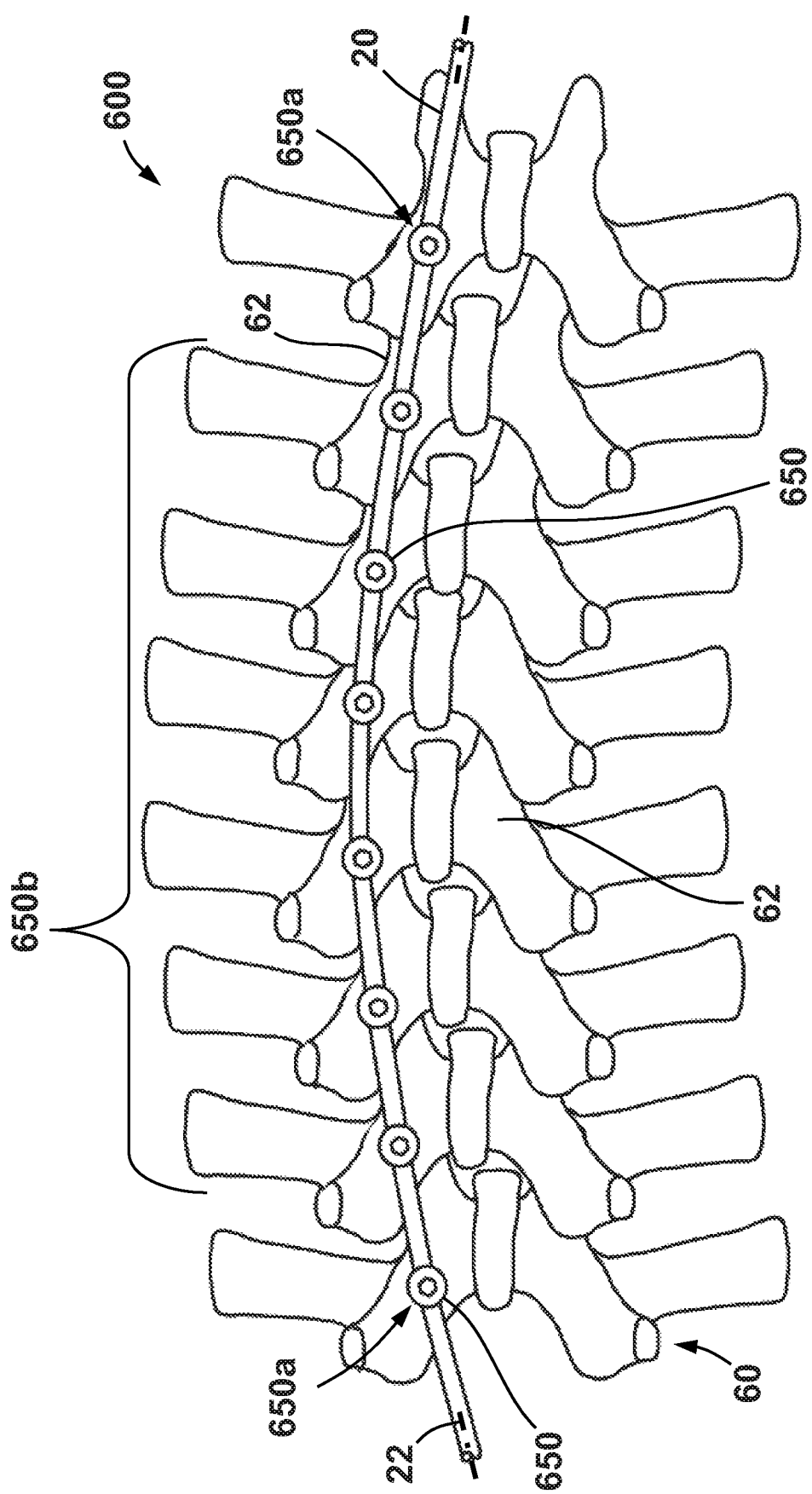
FIG. 10 is a posterior view of another spinal implant system for correcting spinal deformities, according to some embodiments.

Referring now to FIG. 10, another spinal implant system 600 for correcting spinal deformities is shown. System 600 is installed along a posterior aspect of vertebrae 62 rather than the anterior side as described above for system 300 (see FIG. 1). In this embodiment, system 600 is adapted to a posterior surgical approach by including a plurality of anchors 650 coupled to elongate connector 20 (which is the same as previously described above). Anchors 650 are generally the same as anchor 500 shown in FIGS. 7 and 8, except that anchors 650 do not include base 550. However, it should be appreciated that any of the anchors described above may be utilized within system 600 in place of anchors 650 (e.g., anchors 100, 400, or 500) in other embodiments. In addition, as described above for system 300, the plurality of anchors 650 includes a pair of first or outer anchors 650a, and a plurality of second or inner anchors 650b disposed between the outer anchors 650a along the elongate connector 20. Elongate connector 20 is fixably secured (e.g., axially and/or rotationally with respect to axis 22) to outer anchors 650a and is axially and/or rotationally movable relative to inner anchors 650b in the manner previously described above. Thus, system 600 may be utilized to selectively impart desired loads and moments to spine 60 to correct a spinal deformity in substantially the same way as described above for system 300. A posterior surgical approach may be desirable in some embodiments as it may be less invasive of the patient's major body cavities (e.g. abdomen or chest) and may allow for easier access to system 600 for adjustments or removal during a subsequent surgery.

In the manner described, embodiments disclosed herein include systems and methods for correcting spinal deformities that are configured to apply selectively biased loads and moments to the convex curve of a spine (e.g., system 300). Thus, the disclosed systems and methods may provide an option for surgical intervention that does not include spinal fusion. As a result, the disclosed systems and methods may be particularly useful for correcting spinal deformities in children. Broadly speaking, the embodiments disclosed herein include a spinal instrumentation system that can be used in a growing patient to apply corrective forces to the convex aspect of the deformity without requiring spinal fusion.

In some embodiments, set screw 10 may include an axially extending projection (e.g., with respect to axis 15) that is configured to engage with external surface 21 of elongate connector 20 during operations (e.g., such as would be included on a dog point style set screw). In still other embodiments, set screw 10 may be omitted from connection elements 100, and a ligature or other suitable mechanism may be used to engage with elongate connector 20. Additionally, in other embodiments, elongate connector 20 may include one or more crimp detents or local "olives" axially spaced along connector 20 with respect to axis 22. These enlarged or "bulged" regions may exists at a particular positions along the length of elongate connector 20, which may serve as a stop when the enlarged region mates with outer anchors 100a (or outer anchors 650a) or with the plurality of inner anchors 100b (or inner anchors 650b). In some embodiments, the locally enlarged regions can provide enhanced loading stability at the mating union between elongate connector 20 and anchor element 100. In other embodiments, the locally enlarged regions may provide predetermine stop positions along elongate connector 20 that will limit the longitudinal sliding motion relative to each of the plurality of inner anchors 100b. For example, in one specific embodiment, a surgeon may desire a sliding connection between elongate connector 20 and a particular inner anchor 100b, but only until the spine 60 has achieved the target level of curvature correction, such as an arch length difference of X along elongate connector 20 and the associated longitudinal axis 22. The clinician may then mate one of the plurality of inner anchors 100b with elongate connector 20 within the corresponding slot 34. During this process, the clinician may position one of the local "olives" or cross-sectional bulges of the elongate connector 20, the distance of X from inner anchor 100b. This configuration may be advantageous as corrective loads and displacements between vertebrae 62 can be calculated before surgery and the correction assembly 300 can be configured to automatically redistribute loading to other sections of spine 60 as the local "olives" or cross-sectional bulges come to rest against inner anchors 100b.

While exemplary embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. An anchor for a spinal implant system, the anchor comprising:
   a central axis;
   a base comprising:
      a central hub comprising first end, a second end, and a through passage extending axially from the first end to the second end; and
      a plurality of struts coupled to the central hub;
   a head that is configured to be coupled to the base, wherein the head includes a radially extending slot configured to receive an elongate connector therethrough; and
   a threaded portion including a first thread and a second thread, wherein the threaded portion is configured to extend through the through passage from the first end past the second end of the central hub, such that the first thread is configured to engage within a spinal vertebrae to mount the base and the head to the spinal vertebrae, and the second thread is configured to threadably engage with an internal thread within the through passage of the central hub.

2. The anchor of claim 1, comprising a set screw that is configured to threadably engage within the slot of the head to selectively compress the elongate connector against a seat formed within the slot.

3. The anchor of claim 1, wherein the second thread is axially adjacent the first thread and axially between the head and the first thread.

4. The anchor of claim 3, comprising a screw that includes a screw head and the threaded portion, wherein the threaded portion extends from the screw head, and wherein the second thread is disposed between the first thread and the screw head.

5. The anchor of claim 3, comprising a monolithic head assembly that includes the head and the threaded portion.

6. The anchor of claim 1, wherein the base comprises a plate extending radially outward from the central hub that is axially disposed between the first end and the second end of the central hub, and wherein the plurality of struts extend from the plate.

7. The anchor of claim 6, wherein the plurality of struts are biased inward toward a plane containing the central axis.

8. The anchor of claim 6, wherein the base comprises a shape memory material.

9. The anchor of claim 1, wherein engagement of the first thread within the spinal vertebrae is configured to axially compress the second end of the central hub against an external surface of the spinal vertebrae.

10. A spinal implant system for treating a spinal deformity, the system comprising:
   an elongate connector;
   a plurality of anchors configured to be coupled to the elongate connector, wherein each of the plurality of anchors is configured to be mounted to a corresponding vertebrae of a spine;
   wherein each of the plurality of the anchors comprises:
      a central axis;
      a base comprising:

a central hub comprising first end, a second end, and a through passage extending axially from the first end to the second end;
a plate coupled to the central hub; and
a plurality of struts extending from the plate;
a head that is configured to be coupled to the base, wherein the head includes a radially extending slot configured to receive the elongate connector therethrough; and
a threaded portion including a first thread, wherein the threaded portion is configured to extend through the through passage from the first end past the second end of the central hub, such that the first thread is configured to engage within a spinal vertebrae to mount the base and the head to the spinal vertebrae, and the second thread is configured to threadably engage with an internal thread within the through passage of the central hub.

11. The spinal implant system of claim 10, wherein each anchor comprises a set screw that is configured to threadably engage within the slot of the head to compress the elongate connector against a seat formed within the slot.

12. The spinal implant system of claim 10, wherein the plate extends radially outward from the central hub and is axially disposed between the first end and the second end of the central hub.

13. The spinal implant system of claim 12, wherein the base of each anchor comprises a shape memory material.

14. The spinal implant system of claim 12, wherein the second thread is axially adjacent the first thread and axially between the head and the first thread.

15. The spinal implant system of claim 14, wherein each anchor comprises a screw that includes a screw head and the threaded portion, wherein the threaded portion extends from the screw head, and wherein the second thread is disposed between the first thread and the screw head.

16. The spinal implant system of claim 14, wherein each anchor comprises a monolithic head assembly that includes the head and the threaded portion.

17. The spinal implant system of claim 10, wherein for each of the plurality of anchors, an engagement of the first thread within the spinal vertebrae is configured to axially compress the second end of the central hub against an external surface of the spinal vertebrae.

18. A spinal implant system for treating a spinal deformity, the system comprising:
an elongate connector;
a plurality of anchors coupled to the elongate connector, wherein each of the plurality of anchors comprises:
a longitudinal axis;
a base comprising a central hub, a plate extending radially outward from the central hub, and a plurality of struts extending from the plate;
a head including a slot that extends radially through the head with respect to the longitudinal axis; and
a threaded portion including a first thread and a second thread, wherein the threaded portion is configured to extend through a through with an internal thread within the through passage of the central hub and to engage the first thread within a spinal vertebrae;
wherein the plurality of anchors comprises a pair of external anchors, and a set of internal anchors disposed between the external anchors along the elongate connector; and
wherein the elongate connector is fixed within the slot of each of the external anchors and is movable within the slot of each of the internal anchors.

19. The spinal implant system of claim 18, wherein the plurality of struts are biased inward toward a plane containing the longitudinal axis.

* * * * *